(12) United States Patent
Stevens

(10) Patent No.: US 8,678,817 B2
(45) Date of Patent: Mar. 25, 2014

(54) ORTHODONTIC BRACKET WITH SLOT BASE

(76) Inventor: Clarke John Stevens, Omaha, NE (US)

( * ) Notice: Subject to any disclaimer, the term of this patent is extended or adjusted under 35 U.S.C. 154(b) by 0 days.

(21) Appl. No.: 13/234,488

(22) Filed: Sep. 16, 2011

(65) Prior Publication Data

US 2013/0071803 A1 Mar. 21, 2013

(51) Int. Cl.
*A61C 7/12* (2006.01)
(52) U.S. Cl.
USPC .................................. 433/8; 433/16
(58) Field of Classification Search
USPC ............................. 433/8–17, 22, 18
See application file for complete search history.

(56) References Cited

U.S. PATENT DOCUMENTS

| | | | | |
|---|---|---|---|---|
| 3,438,132 A | * | 4/1969 | Rubin | 433/11 |
| 4,582,487 A | * | 4/1986 | Creekmore | 433/8 |
| 4,917,602 A | * | 4/1990 | Broussard | 433/8 |
| 5,044,945 A | * | 9/1991 | Peterson | 433/8 |
| 5,160,261 A | * | 11/1992 | Peterson | 433/8 |
| 5,299,934 A | * | 4/1994 | Suyama | 433/8 |
| 5,302,121 A | * | 4/1994 | Gagin | 433/10 |

* cited by examiner

*Primary Examiner* — Cris L Rodriguez
*Assistant Examiner* — Edward Moran
(74) *Attorney, Agent, or Firm* — Rodgers & Rodgers

(57) ABSTRACT

The present invention provides an improved orthodontic bracket. According to one embodiment, the orthodontic bracket includes a mounting base for attachment to a tooth surface and an archwire slot formed upon the base and sized for receiving an orthodontic archwire. The bracket body has a facially curved slot lingual sidewall that causes the archwire to contact the bracket body. The bracket embodiment has a mesial and distal convexity contoured bracket base and slot lingual sidewall such that there is no contact by an archwire when an archwire is placed in an aligned dental arch. Additional features of the improved design are occlusal and gingival convex contouring of the tie wings such that there are no sharp corners on the archwire slot.

1 Claim, 5 Drawing Sheets

ORTHODONTIC BRACKET WITH SLOT BASE

FIELD OF THE INVENTION

The present invention provides an improved orthodontic bracket. According to one embodiment, the orthodontic bracket includes a mounting base for attachment to a tooth surface and an archwire slot formed upon the base and sized for receiving an orthodontic archwire. The bracket body has a facially curvilinear lingual bracket wall that causes the archwire to contact the bracket body. The bracket embodiment has a mesial and distal convexity contoured bracket base and sidewall such that there is no contact by an archwire when an archwire is placed in an aligned dental arch. Additional features of the improved design are occlusal and gingival convex contouring of the tie wings such that there are no sharp corners on the archwire slot.

BACKGROUND OF THE INVENTION

The present invention relates to an apparatus and method for orthodontic treatment. The embodiment of the orthodontic bracket designed consists of two tie wings or projections which form a rectangular slot or groove. The slot is designed to hold the wire which connects all of the teeth in a dental arch. The tie wings typically hold the archwire by means of a wire or elastic ligature. The twin bracket has proven to be an excellent way to move teeth in three planes of space. The specific movements are rotation, vertical change, and torque. The two tie wings help facilitate the rotation of the tooth. The slot in each of the tie wings allows for movement of teeth vertically and also allows for tipping of the root or crown. The slot is rectangular so as to be able to accommodate a rectangular wire which allows an individual tooth to be moved in a third dimension that torques or tips the root of the tooth.

The orthodontic bracket appliance that is in common use today began with gold brackets soldered to gold bands that were cemented around each tooth. The dimension of the slot was 0.022 inch (height) by 0.028 inch (depth). Gold wires and bands were abandoned in the 1950s and were replaced with stainless steel. Because gold is a softer metal than stainless steel, manufacturers developed bracket slots of 0.018 inch by 0.028 inches to accommodate the stiffer stainless steel wires. This change in wire size was required to duplicate the forces produced by the softer gold wires.

Orthodontists were reluctant to abandon the 0.022 slot out of tradition. As a result, orthodontic brackets are still manufactured in two slot sizes. Most manufacturers offer both 0.022 slot and 0.018 slot orthodontic brackets. The common method of manufacturing the two sizes of slots is to cast a bracket that can be cut to both bracket sizes. When metal injection molding is used, it only produces one bracket size.

When using the 0.022 slot twin brackets, orthodontists begin treatment with small round archwires ranging in size from 0.014 inch to 0.020 inch. Treatment is initiated with small archwires which are flexible and facilitate the easy rotation and vertical movement of teeth. The round archwires are followed by rectangular archwires. The rectangular archwires are used in finishing treatment and provide for proper torque and angulation. These finishing archwires are usually of the rectangular dimension, 0.022 inch by 0.025 inches. The final archwires are placed with several bends, specifically made to move each tooth to its ideal position. In the 1970's inta "straight-wire" bracket was introduced. It was fashioned to eliminate the need for the many bends in the finishing wires. The bracket slots had different rotations, tips, and torque for each tooth, essentially a prescription for each tooth.

The larger slot size works more efficiently in the early stages of treatment because it minimizes friction and binding forces when used with round archwires. The smaller slot size works best with the finishing wires because a finishing wire of 0.018 inch by 0.022 inches is not as stiff as a finishing wire of 0.022 inch by 0.025 inches. The larger archwire is so inflexible it is almost impossible to place in the mouth. Most orthodontists use a finishing archwire of 0.018 inch by 0.022 inches. If the finishing wire does not fill the slot, then the wire does not produce the precise movement required. Orthodontic brackets have been unable to take full advantage of the significant changes in dental materials such as nickel-titanium and titanium-molybdenum archwires developed in the 1990's. Manufacturers have focused on adding features to existing bracket slot designs such as selfligating doors to reduce some of the friction. The nickel-titanium archwires are flexible and more resilient and can consequently aid in reducing binding forces. The accuracy of metal injection molding and the advances in archwire technology drive the innovative changes that have been incorporated in the present invention.

SUMMARY OF THE INVENTION

In accordance with one embodiment of the present invention, an orthodontic twin bracket is provided which includes a mesial occlusal tie wing, a distal occlusal tie wing, a mesial gingival tie wing, a distal gingival tie wing, and an archwire slot having a slot lingual sidewall and two archwire sidewalls formed by the tie wings.

The orthodontic bracket slot lingual sidewall is convex with a radius which causes the archwire to contact the bracket slot lingual sidewall along only one point on the convexity of the slot lingual sidewall.

Further, the slot dimensions may differ in various embodiments of the invention.

The orthodontic bracket further includes a mesial occlusal tie wing that extends to the gingival in a radius so as to contact the archwire along only one line of the convexity.

The orthodontic bracket further includes a distal occlusal tie wing that extends to the gingival in a radius so as to contact the archwire along only one line of the convexity.

The orthodontic bracket further includes a mesial gingival tie wing that extends to the occlusal in a radius so as to contact the archwire along only one line of the convexity.

The orthodontic bracket further includes a distal occlusal tie wing that extends to the occlusal in a radius so as to contact the archwire along only one line of the convexity.

BRIEF DESCRIPTION OF THE DRAWINGS

The above and other objects, features, and advantages of the invention will be better understood from the following detailed description with the accompanying drawings.

DETAILED DESCRIPTION OF THE INVENTION

Figure 1:
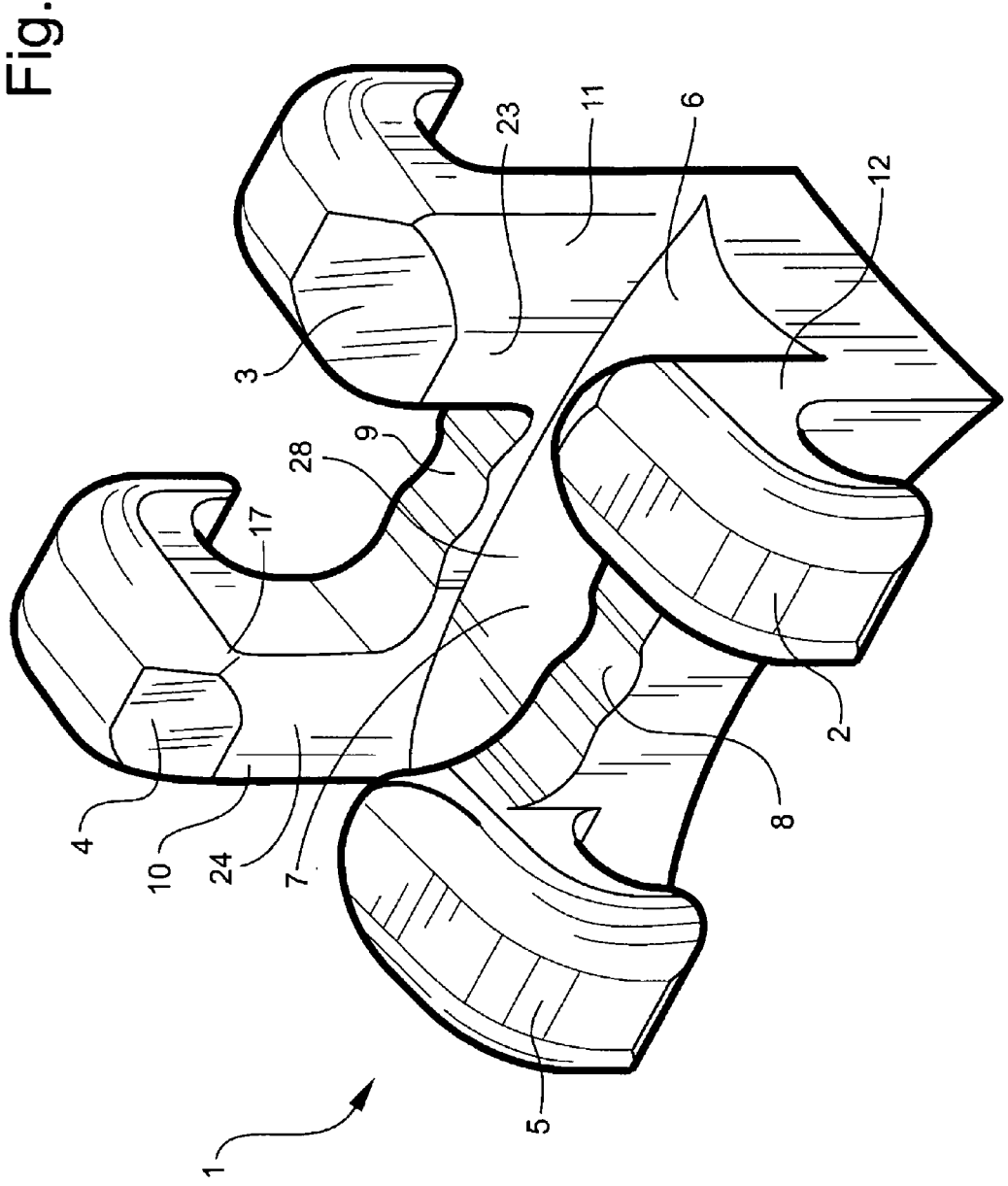
FIG. 1 is a perspective view illustrating an orthodontic bracket in accordance with an embodiment of the current invention.

The embodiments of the invention are described with reference to the accompanying drawings.

Many different forms and embodiments are possible without deviating from the scope of this disclosure and so the disclosure should not be construed as limited to the example embodiments set forth herein. Rather, these example embodiments are provided so that this disclosure will be thorough and complete and will convey the full scope of the disclosure to those skilled in the art.

The sizes and relative sizes of layers and regions may be exaggerated for clarity in the drawings.

It will be understood that when an element or layer is referred to as being "on," "connected to," or "coupled to" another element or layer, it can be directly on, connected, or coupled to the other element or layer or intervening elements or layers may be present. In contrast, when an element is referred to as being "directly on," "directly connected to," or "directly coupled to" another element or layer, there are no intervening elements or layers present. Like numbers refer to like elements throughout. As used herein, the term "and/or" includes any and all combinations of one or more of the associated listed items.

The terminology used herein is for the purpose of describing example embodiments only and is not intended to be limiting. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The terms (including technical and scientific terms) used herein have the same meaning as commonly understood by one skilled in the art to which this disclosure pertains. It will be further understood that terms such as those defined in commonly used dictionaries, should be interpreted as having a meaning that is consistent with their meaning in the context of the relevant art and will not be interpreted in an idealized or overly formal sense unless expressly so defined herein.

The present invention will be described in accordance with accompanying Figures.

FIG. 1 illustrates a perspective view of the facial side of the orthodontic twin bracket 1 in accordance with the present invention. The bracket 1 includes a mesial occlusal tie wing 2, distal occlusal tie wing 5, mesial gingival tie wing 3, and distal gingival tie wing 4. Located between the gingival tie wings 3 & 4 and the occlusal tie wings 2 & 5 is a mesial to distal extending archwire slot 28. The archwire slot 28 includes an slot lingual sidewall that is curvilinear and point of archwire contact 7, a gingival sidewall, and an occlusal sidewall. The tie wings are convex with the apex of the tie wing radius on the mesial/gingival tie wing 23 and on the distal/gingival tie wing 24. FIG. 1 shows a mesial convexity 12 on the mesial/occlusal tie wing, a mesial convexity 11 on the mesial/gingival tie wing, a mesial convexity 17 on the distal/gingival tie wing, and a distal convexity 10 on the distal/gingival tie wing. The slot lingual sidewall is convex on the mesial aspect 6. Located between the wings are concave lingual depressions on the occlusal 8 and gingival 9 aspects.

Figure 2:
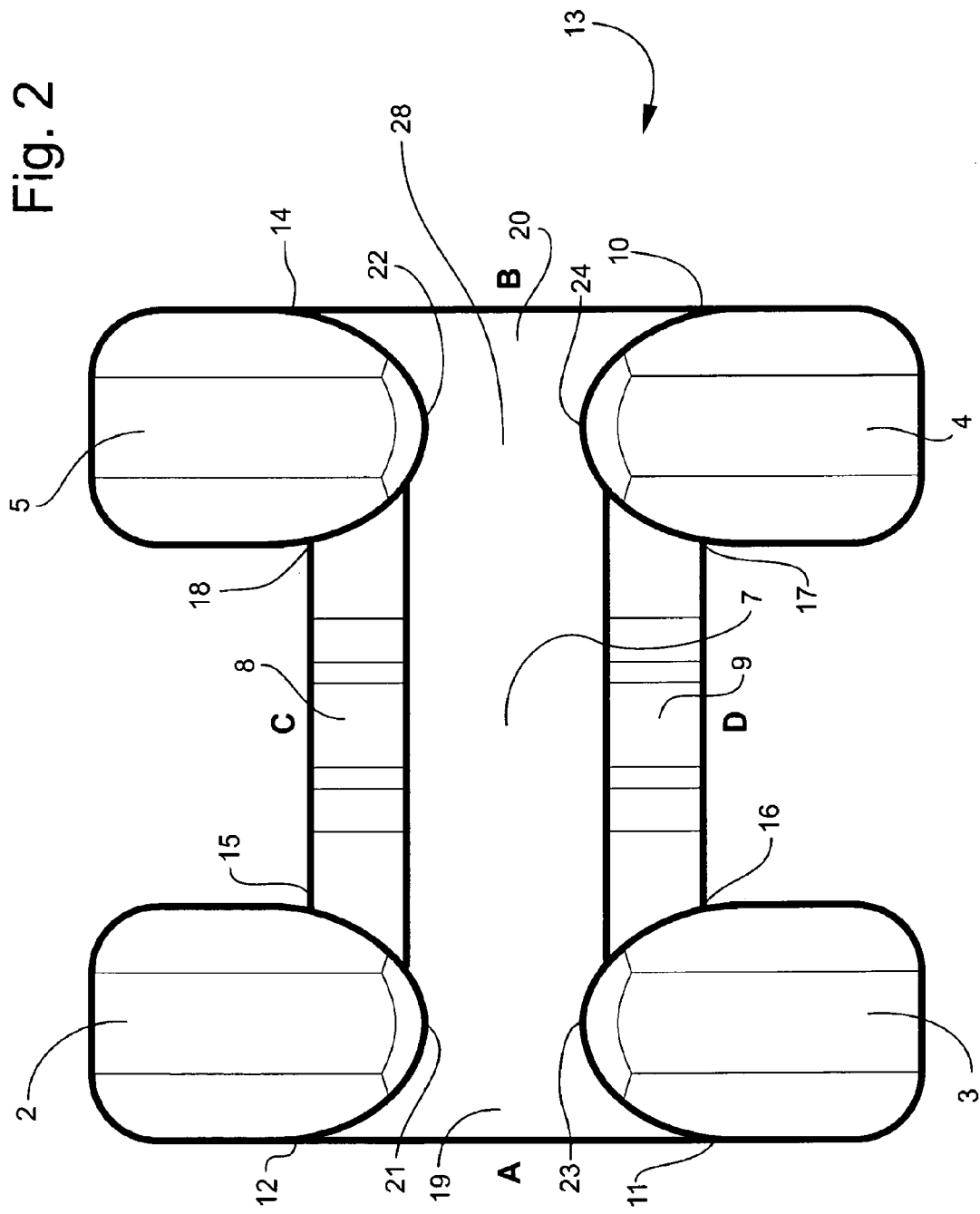
FIG. 2 is a front view illustrating an orthodontic bracket in accordance with an embodiment of the current invention.

FIG. 2 illustrates a facial view 13 of the bracket in accordance with the present invention. The convex tie wings, mesial/occlusal 2, mesial/gingival 5, distal/gingival 4, and distal/gingival 3 are convex on the surface which touches the archwire. The predominant manufacturing produces orthodontic brackets that have flat slot lingual sidewalls and contact the archwire along the entire surface of the slot rather than one point on a convex curvilinear slot surface 7. It is commonly known that friction is minimized when the contact of two objects sliding across one another is reduced. Another factor which reduces the efficacy of archwire movements in twin brackets is binding force. There have been studies showing notching of archwires when archwires bind the tie wings during placement of the archwires. The convex bracket tie wings 21, 22, 23, and 24 should greatly reduce the friction and binding forces. Metal injection molding is uniquely suited to produce an accurate convex surface on the tie wing. Current technology of cutting the archwire slot does not allow for production of the convex tie wing. The convex distal aspects of the distal/occlusal 2 and distal/gingival tie wings 14 & 10 and convex mesial aspects of the mesial/occlusal and mesial/gingival tie wings 11 & 12 reduce binding.

Figure 3:
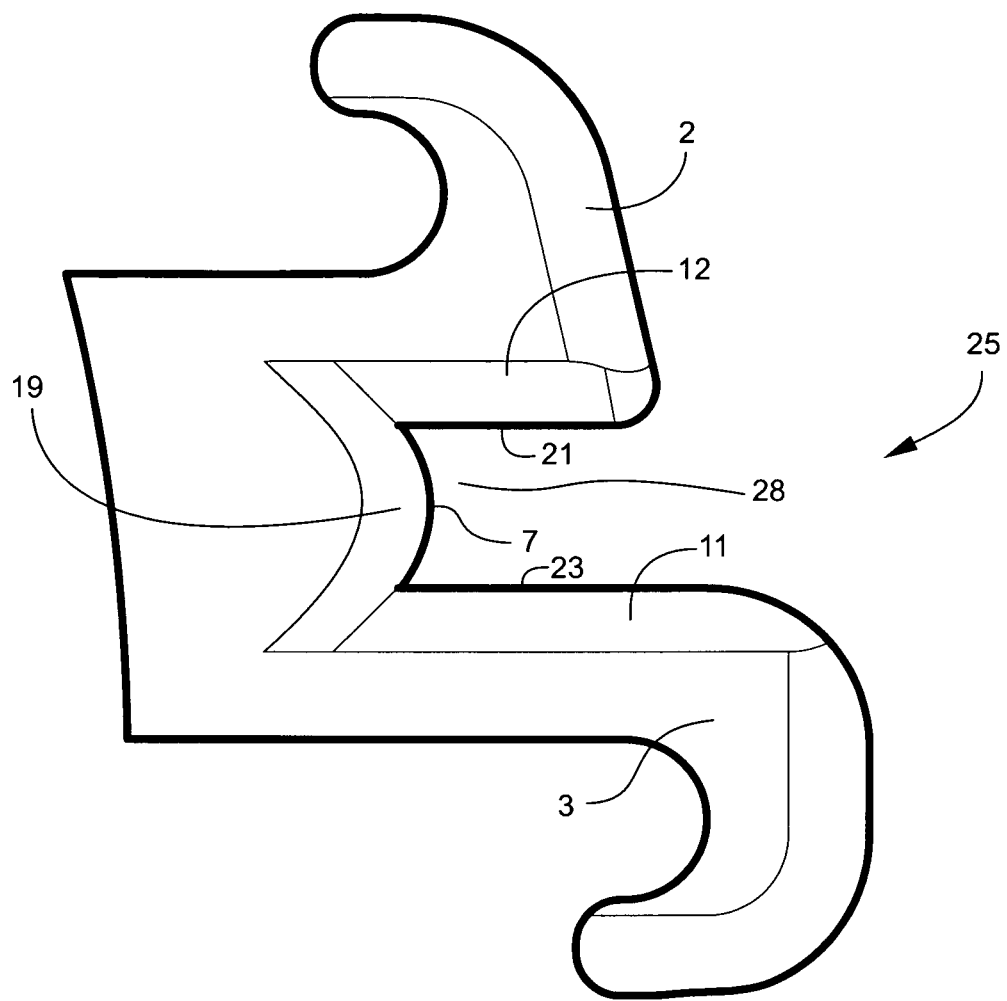
FIG. 3 is a mesial side view illustrating an orthodontic bracket in accordance with an embodiment of the current invention.

FIG. 3 illustrates a side view of the orthodontic bracket in accordance with the current embodiment of the invention. The bracket will have a slot size that is variable in both the occlusal gingival and facial lingual dimension 28. A crucial aspect in reducing friction and binding forces is the contact of the wire with the archwire slot floor, or lingual surface of the bracket slot. There are a variety of available designs that are used for the lingual surface or the bracket slot floor. Some designs are continuous from mesial to distal and some are split in the middle between the tie wings. The orthodontic bracket in the current invention is designed to have the archwire contact the lingual surface of the slot at one point 7, minimizing friction. The slot lingual sidewall is convex in the occlusal to gingival aspect illustrated by the convexity 7. The binding force between the tie wings of the adjacent teeth would be reduced because there would be less binding on the edge of the slot on the mesial 19 and distal 20 aspects of the orthodontic bracket slot lingual sidewall. The mesial 19 and distal 20 aspects of the lingual surface of the slot will be convex so as to not allow notching or binding of the archwire. Metal injection molding is required to produce the convex lingual slot surface 7 and convex mesial 19 and distal 20 aspects of the slot. The current technology which cuts the slot only leaves a flat lingual surface and sharp corners on the mesial and distal aspects of the slot.

Figure 4:
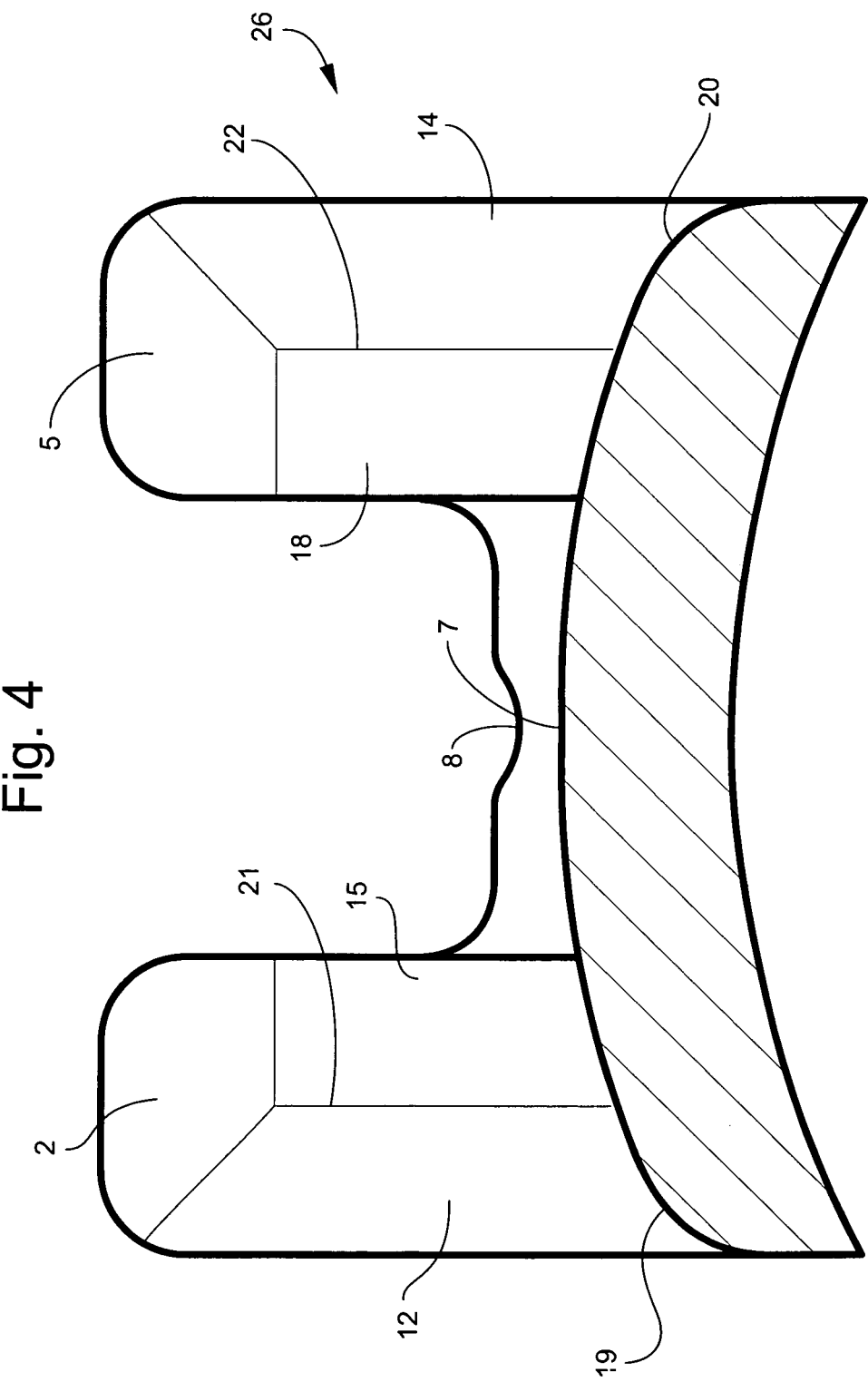
FIG. 4 is a cutaway view taken along with A-B line of FIG. 2 in accordance with an embodiment of the current invention.

FIG. 4 is a cutaway view of the orthodontic bracket illustrating the mesial occlusal 2 and distal occlusal 5 tie wings taken as seen from the gingival 26. It shows the most convex part of the slot lingual sidewall 7 and the mesial 19 and distal 20 convexities of the slot lingual sidewall. The convex slot lingual sidewall 7, 19, and 20 illustrated in the cutaway view of FIG. 4 will reduce archwire binding in the facial lingual plane. The convexity of the present invention is a continuous convexity, not a single convex projection or interruption in the slot lingual sidewall.

Figure 5:
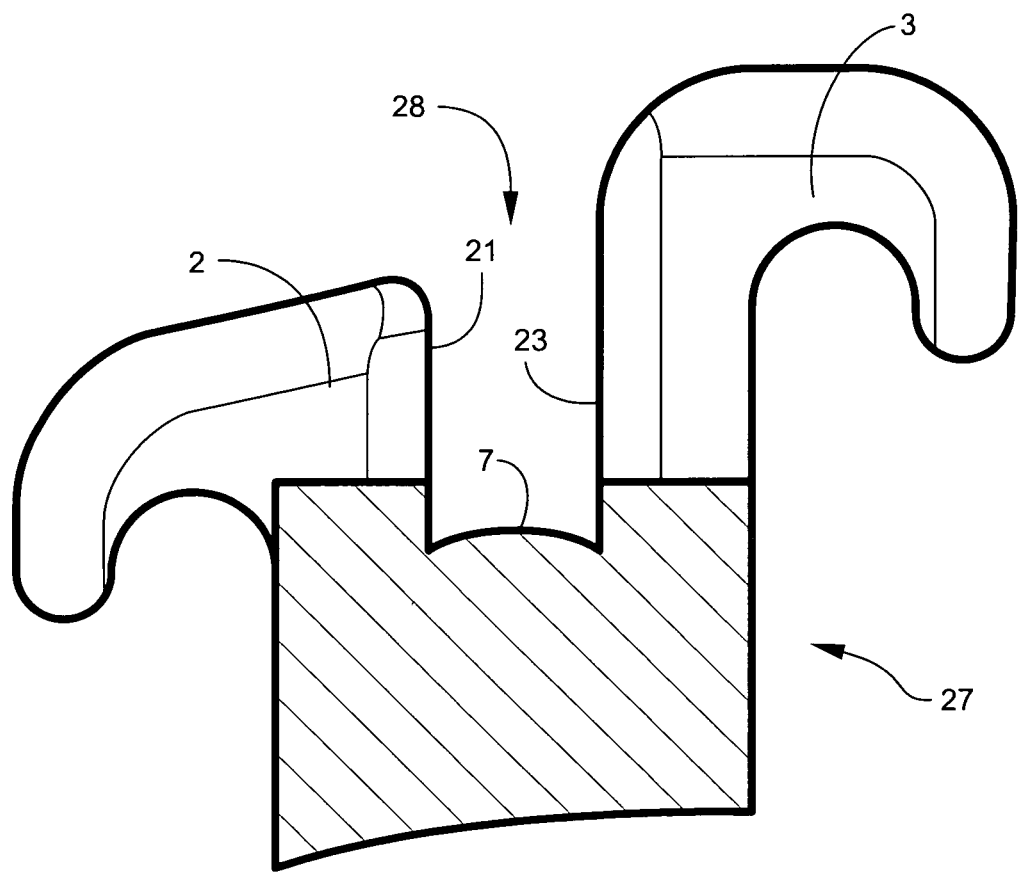
FIG. 5 is a cutaway view taken along the C-D line of FIG. 2 in accordance with an embodiment of the current invention.

FIG. 5 is a cutaway view illustrating the orthodontic bracket from the midline 27 with a view of the mesial occlusal bracket 2 and the mesial gingival bracket 3 from the distal. The archwire slot 28 occlusal gingival dimension is shown and is located between the gingival convexity 21 of the occlusal tie wing and the occlusal convexity 23 of the mesial gingival tie wing. The most convex aspect 7 of the slot lingual sidewall is illustrated. The occlusal 8 and gingival 9 concave lingual depressions representing the long axis of the tooth are also illustrated.

What is claimed is:

1. An improved orthodontic appliance comprising a mounting base for attachment to a tooth surface, a bracket upstanding from said base, an archwire slot formed in said bracket for receiving an orthodontic archwire, said archwire having a top wall, a bottom wall, and opposed sidewalls, said archwire slot including spaced ends at a mesial and distal outer edge of the bracket and spaced occlusal and gingival sidewalls, at least one pair of tie wings extending upwardly from said mounting base, said slot including a lingual sidewall curving continuously convexly in the vertical and horizontal planes between said ends and between said archwire slot sidewalls forming an apex point of the lingual sidewall at the center of the bracket and archwire slot, the contact between said archwire and said lingual sidewall being a minimum amount of touching at said apex point on said lingual sidewall, said tie wings comprising surfaces curved convexly in the vertical and horizontal planes, said tie wings surfaces extending into said archwire slot to define opposing apexes in said occlusal and gingival sidewalls of the archwire slot, and wherein the only points of contact between said archwire bottom wall and sidewalls and said bracket are said apexes on the lingual, occlusal and gingival sidewalls of the archwire slot when said archwire is disposed in said slot.

* * * * *